United States Patent [19]

Eigtved

[11] Patent Number: 5,156,963
[45] Date of Patent: Oct. 20, 1992

[54] IMMOBILIZATION OF LIPASE BY ADSORPTION ON A PARTICULATE MACROPOROUS RESIN

[75] Inventor: Peter Eigtved, Holte, Denmark

[73] Assignee: Novo Nordisk A/S, Bagsvaerd, Denmark

[21] Appl. No.: 469,510

[22] PCT Filed: Sep. 28, 1999

[86] PCT No.: PCT/DK88/00158
§ 371 Date: Mar. 28, 1990
§ 102(e) Date: Mar. 28, 1990

[87] PCT Pub. No.: WO89/02916
PCT Pub. Date: Apr. 6, 1989

[30] Foreign Application Priority Data

Sep. 28, 1987 [DK] Denmark .............................. 5072/87
Dec. 28, 1987 [DK] Denmark .............................. 6872/87

[51] Int. Cl.$^5$ .......................... C12P 7/62; C12P 7/64; C12N 11/08
[52] U.S. Cl. .................................... 435/135; 435/134; 435/180; 435/874; 435/921; 435/931
[58] Field of Search ............... 435/134, 135, 174, 177, 435/180, 874, 921, 931

[56] References Cited

U.S. PATENT DOCUMENTS

| | | | |
|---|---|---|---|
| 4,338,398 | 7/1982 | Yoneyama | 435/180 X |
| 4,472,503 | 9/1984 | Matsuo et al. | 435/180 X |
| 4,798,793 | 1/1989 | Eigtved | 435/134 |
| 4,818,695 | 4/1989 | Eigtved | 435/134 |
| 4,898,822 | 2/1990 | Asada et al. | 435/180 X |

*Primary Examiner*—David M. Naff
*Attorney, Agent, or Firm*—Steve T. Zelson; Elias J. Lambiris

[57] ABSTRACT

Lipase is immobilized by adsorption on a polymethacrylic acid ester resin such as polymethylmethacrylate cross-linked with divinyl benzene. The resin is preferably a particulate, macroporous resin having an average pore radius of 100–200 Å, a total surface area of 25–150 m$^2$/g and a particle size of 100–1,000 μm. The lipase may be obtained from *Mucor miehei, Candida antarctica, Pseudomonas cepacia* or *Humicola lanuginosa*. The immobilized lipase may be dried and is used for interesterifying an ester, hydrolyzing an ester or synthesizing an ester. Interesterification can be carried out continuously in a fixed-bed column.

10 Claims, 1 Drawing Sheet

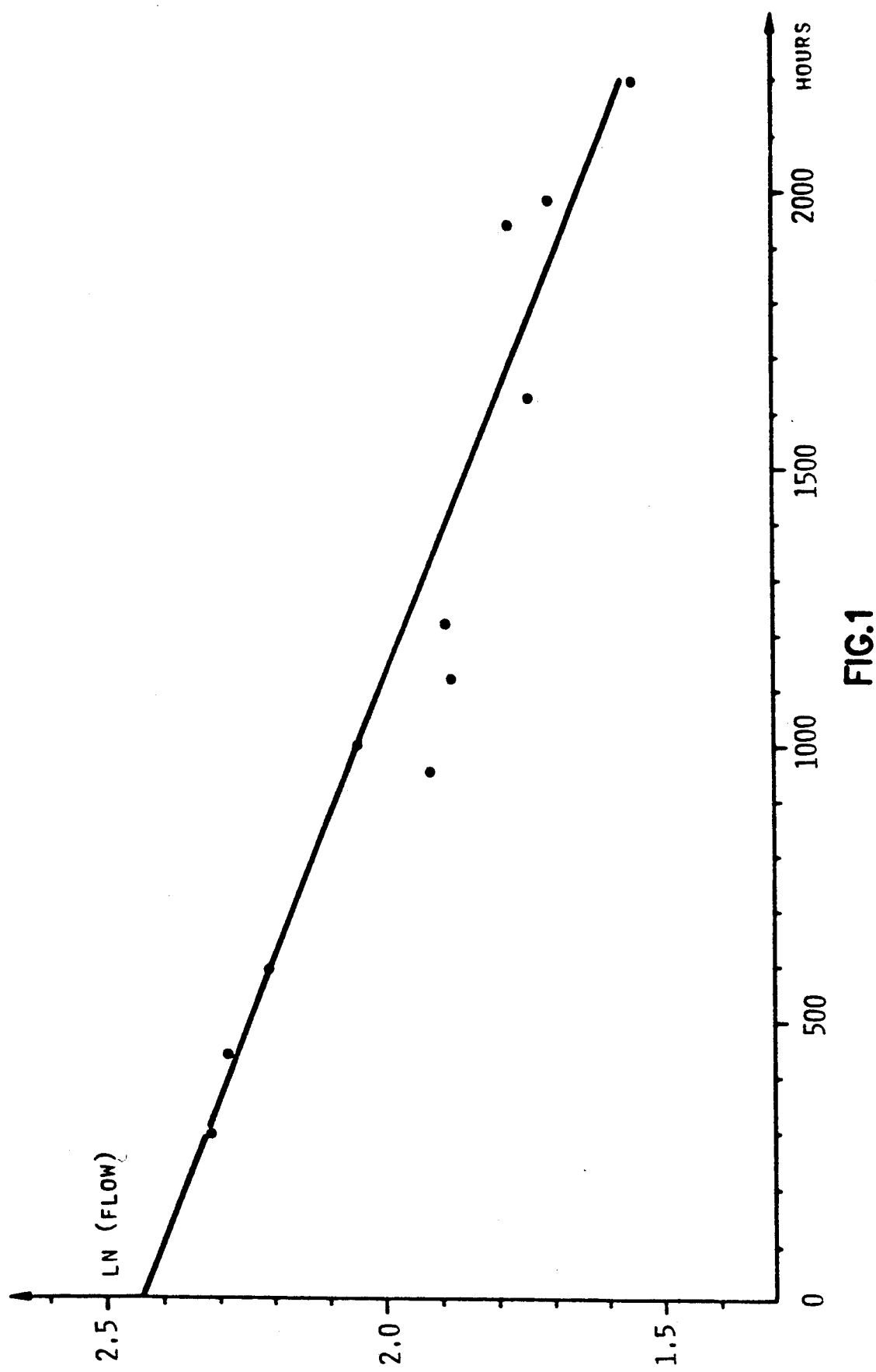

IMMOBILIZATION OF LIPASE BY ADSORPTION ON A PARTICULATE MACROPOROUS RESIN

This invention relates to a method for immobilizing lipase, to an immobilized lipase preparation and to use of the immobilized lipase.

BACKGROUND ART

Various immobilization methods for lipase are known. Thus, EP 140,542 (Novo) discloses immobilization of Mucor lipase by adsorption on a weakly basic anion exchange resin, and DK 85/878 (Novo) discloses immobilization of the same lipase on adsorbent resin of phenol-formaldehyde type.

Kimura et. al., Eur. J. Appl. Microbiol. Biotechnol. (1983) 17:107-112 discloses Candida lipase immobilized by adsorption on phenol-formaldehyde resins of various functionality.

STATEMENT OF THE INVENTION

We have surprisingly found that immobilization of lipase on a macroporous adsorbent resin of the acrylic type leads to a product with higher interesterification activity than prior-art methods, even when the same amount of native lipase is used in the two methods. This immobilization method is applicable to a wide variety of microbial lipases from bacteria, yeasts or fungi, including both 1,3-specific and positionally non-specific lipases. All these lipases immobilized by said method have good interesterification activity and enhanced thermostability compared to the native lipase.

Accordingly, the invention provides a method for immobilizing lipase, characterized by adsorption of the lipase on a particulate, macroporous adsorbent resin of the acrylic type.

The invention also provides an immobilized lipase preparation, characterized in that the lipase is adsorbed on a particulate, macroporous resin of the acrylic type.

Further, the invention provides use of said immobilized lipase in interesterification, ester synthesis and ester hydrolysis.

DETAILED DESCRIPTION OF THE INVENTION

Resin

Typical resins for use in the invention consist of poly(meth)acrylic acid esters, (e.g. poly-methyl methacrylate) crosslinked with divinyl benzene. They are macroporous and typically have average pore radius about 100-200 Å and a total surface area of 25-150 m$^2$/g (by N$_2$ adsorption method).

For use in continuous interesterification in a fixed-bed column the particles should preferably be spherical and of uniform size, preferably 100-1000 μm, e.g. 100-500 μm.

Examples of resins are Lewatit ® E 2001/85 (Bayer, West Germany), Amberlite ® XAD-8 (Rohm & Haas, USA).

Immobilization process

The immobilization is conveniently carried out simply by contacting an aqueous solution of the lipase with the resin, thereafter separating the thus formed immobilized lipase from the aqueous phase followed by washing and drying of the separated immobilized lipase.

Suitable temperature and pH will depend on the characteristics of the lipase, but in many cases ambient temperature and pH near neutral may conveniently be used.

Contact time will usually be chosen as needed for essentially complete adsorption. This will typically be from 1-2 hours up to 24 hours.

Microbial lipase

The lipase to be immobilized is preferably microbial. Some preferred lipases are derived from the following organisms:

Mucor sp., especially M. miehei, commercially available as Lipozyme ® (Novo)

Candida sp., especially C. rugosa (available from Meito Sangyo, Japan, as Lipase OF) and C. antarctica, see PCT/DK87/00127 (Novo).

Pseudomonas sp., especially Ps. cepacia, see DK 87/3993 (Novo).

Humicola sp., especially H. lanuginosa, see JP 53-45,394B (Arima), DK 4499/87 (Novo) and JP 62-79,782A (Unitika).

Lipase-catalyzed processes

The immobilized lipases of the invention can be used in ester hydrolysis, ester synthesis and interesterification. The latter term includes acidolysis (reaction of ester+acid), alcoholysis (ester+alcohol) and transesterification (ester+ester). Besides triglycerides, other esters may be used depending on substrate specificity of the lipase.

The immobilized lipases of the invention are particularly useful for continuous interesterification in a fixed-bed column.

BRIEF DESCRIPTION OF THE DRAWINGS

FIG. 1 shows the results of continuous acidolysis. Details are given in Example 2.

EXEMPLARY PRACTICE OF THE INVENTION

Assays for activity of soluble lipase (LU)

The method is based on hydrolysis of tributyrine in a pH-stat. 1 LU (Lipase Unit) is the amount of enzyme which liberates 1 μmol titratable butyric acid per minute at 30° C, pH 7.0 with gum arabic as an emulsifier. Further details are given in Novo Analytical Method AF 95/5, available on request.

Acidolysis activity of immobilized lipase (BIU)

The activity is determined by reacting palmitic acid with triolein with or without solvent Total incorporation of palmitic acid is measured by FAME-GLC of triglyceride.

FAME-GLC (Fatty acid methyl ester—gas-liquid chromatography) may be done according to methods Ce 2-66 and Ce 1-62 published by the American Oil Chemists' Society (AOCS).

In case of reaction with solvent, the reaction mixture consists of 0.6 g of triolein, 0.174 g of palmitic acid and 8.083 g of petroleum ether. For reaction without solvent, 3.0 g of triolein and 0.87 g of palmitic acid is used.

In either case, a suitable amount of enzyme is hydrated, incubated with the above reaction mixture at a given temperature for 1-4 hours, and then filtering to stop the reaction. The filtrate is purified on an alumina column, and the triglycerides are analyzed by FAME-GLC.

One BIU (Batch Interesterification Unit) is the amount of immobilized lipase that incorporates palmitic acid at an initial rate of 1 μmole/minute at the given temperature with or without solvent.

EXAMPLE 1

Immobilization of lipases on Lewatit ® E 2001/85

In general an aqueous solution of a given lipase was mixed by rotation with the resin (in this case Lewatit ® E2001/85, product of Bayer) at fixed pH, at room temperature. Then the resin with immobilized lipase was collected by filtration, followed by washing with water and drying in vacuum. The removal of adsorbed lipase was calculated from the hydrolytic lipase activity left in the filtrates (LU-assay). The interesterification activity of the immobilized preparations was measured by the BIU-assay, at 60° C. without solvent.

Data and results are summarized in the following table.

| Source | Lipase Activity (LU/mg) | Lipase Amount (g) | Lipase solution (g) | Lewatit ® E2001/85 resin D.S. (g) | pH | Time (h) | Lipase removal (%) | Load (LU/mg) | Activity/ 60° C. (BIU/g) |
|---|---|---|---|---|---|---|---|---|---|
| Mucor | 112 | 2.6 | 25 | 8.5 | 6.1 | 21 | 99 | 33 | 171 |
| Candida | 221 | 3.4 | 60 | 25 | 7.4 | 23 | 98 | 30 | 60 |
| Pseudomonas | 12.6 | 59 | 59 | 25 | 6.9 | 19 | 99 | 32 | 191 |
| Humicola | 211 | 0.71 | 13 | 4.3 | 5.6 | 6 | 93 | 33 | 226 |

Typical results obtained with Mucor lipase on macroporous phenolic resins are loads of approx. 30 LU/mg with activities of approx. 30 BIU/g cf. EP 140,542. With *Candida antarctica* lipase on macroporous phenolic resins loads are below 10 LU/mg and activities are small: 5 BIU/g.

Lewatit ® E 2001/85

This resin is a macroporous, non-ionic adsorbent resin of the polyacrylate type. The average pore radius is around 100 Å and total surface area around 80 m²/g.

Source of lipases from above table

*Mucor miehei*, 1,3-specific (Novo, ref. DK 4234/77)
*Candida antarctica*, non-specific (Novo, ref. PCT/DK87/00127)
*Pseudomonas cepacia*, non-specific (Novo, ref. DK 3993/87)
*Humicola lanuginosa*, 1,3-specific (Novo, ref. DK 4499/86)

EXAMPLE 2

Continuous acidolysis 4.5 g of the immobilized Mucor lipase (Example 1) was filled into a water jacketed column, having an internal diameter of 1.5 cm.

The column was equipped with a water jacket with 0 hot circulating water and was kept at 60° C. A precolumn containing water-saturated resin, (Duolite ® ES561) was placed before the enzyme column and kept at the same temperature. A substrate consisting of 71% highly refined soy bean oil with a peroxide value less than 3 and 29% analytical grade lauric acid was pumped through the columns. At the outlet from the enzyme column samples were taken for analysis, and the incorporation of lauric acid measured by GLC. An incorporation of 14% w/w lauric acid was attempted and the flow rate was adjusted in order to keep the conversion at that value. Measurements of flow rate were taken when the actual conversion was 14±1%. Whenever the precolumn was dry it was replaced by a fresh one.

The samples were analysed by removing the free fatty acid and mono- and diglyceride by Al₂O₃-column chromatography, thereafter methylation of the triglyceride by NaOCH₃ and finally analysis of the methylester on a GLC.

The results, shown in FIG. 1 as the natural logarithm of flow rate (g triglyceride/hour/g immobilized enzyme) versus time (hours), indicate a half-life of about 1,800 hours at 60° C.

EXAMPLE 3

Immobilization of lipases on Amberlite ® XAD-8

Immobilizations were carried out basically as described in Example 1. Data and results are summarized in the following table.

| Source | Lipase Activity (LU/mg) | Lipase Amount (g) | Lipase solution (g) | Amberlite ® XAD-8 resin D.S. (g) | pH | Time (h) | Lipase removal (%) | Load (LU/mg) | Activity (BIU/g) | Temp. (°C.) |
|---|---|---|---|---|---|---|---|---|---|---|
| Mucor | 26.8 | 5.0 | 13 | 4.3 | 6.1 | 21 | 99 | 58 | 20 | 40 |
| Humicola | 103 | 1.9 | 12 | 4.0 | 5.0 | 18 | 98 | 44 | 17 | 40 |
| Candida | 210 | 0.95 | 12 | 4.0 | 7.0 | 18 | 93 | 41 | 16 | 60 |

Amberlite ® XAD-8

This resin is a macroporous, non-ionic adsorbent resin of the polyacrylate type. The average pore radius is around 120 Å and total surface area around 140 m²/g.

I claim:

1. A method for immobilizing a lipase comprising adsorption of the lipase on a particulate, macroporous resin of polymethylmethacrylate cross-linked with divinyl benzene having an average pore radius of about 100–200 Å, a total surface area of 25–150 m²/g and a particle size of 100–1,000 μm.

2. The method according to claim 1, wherein the immobilization of the lipase comprises (a) contacting an aqueous solution of the lipase with the resin; (b) separating the immobilized lipase from the aqueous phase; and (c) washing and drying of the immobilized lipase.

3. The method according to claim 1, wherein the lipase is derived from a microorganism genus selected from the group consisting of *Mucor, Candida, Pseudomonas* and *Humicola*.

4. The method according to claim 3, wherein the lipase is derived from a microorganism species selected from the group consisting of *Mucor miehei, Candida antarctica, Pseudomonas cepacia* and *Humicola lanuginosa*.

5. A lipase which is immobilized by the method according to any of the claims 1-4.

6. A method comprising (a) interesterifying an ester with an acid, an alcohol or another ester, (b) hydrolyzing an ester or (c) synthesizing an ester, in the presence of an immobilized lipase, wherein the lipase is immobilized by adsorption on a particulate, macroporous resin of polymethylmethacrylate cross-linked with divinyl benzene having an average pore radius of about 100-200 Å, a total surface area of 25-150 $m^2/g$ and a particle size of 100-1,000 μm.

7. The method according to claim 6, wherein the immobilization of the lipase comprises (a) contacting an aqueous solution of the lipase with the resin; (b) separating the immobilized lipase from the aqueous phase; and (c) washing and drying of the immobilized lipase.

8. The method according to claim 6 or 7, wherein the lipase is derived from a microorganism genus selected from the group consisting of *Mucor, Candida, Pseudomonas* and *Humicola*.

9. The method according to claim 8, wherein the lipase is derived from a microorganism species selected from the group consisting of *Mucor miehei, Candida antarctica, Pseudomonas cepacia* and *Humicola lanuginosa*.

10. The method according to claim 6, wherein the method is interesterification which is carried out continuously in a fixed-bed column.

* * * * *